US011357388B2

(12) United States Patent
Lawrenson et al.

(10) Patent No.: US 11,357,388 B2
(45) Date of Patent: Jun. 14, 2022

(54) MEDICAL IMAGING SYSTEM, METHOD AND COMPUTER PROGRAM

(71) Applicant: Sony Corporation, Tokyo (JP)

(72) Inventors: Matthew Lawrenson, Bussigny (CH); Christopher Wright, London (GB); Naoyuki Hirota, Stuttgart (DE)

(73) Assignee: SONY CORPORATION, Tokyo (JP)

(*) Notice: Subject to any disclaimer, the term of this patent is extended or adjusted under 35 U.S.C. 154(b) by 101 days.

(21) Appl. No.: 16/619,492

(22) PCT Filed: May 28, 2018

(86) PCT No.: PCT/JP2018/020345
§ 371 (c)(1),
(2) Date: Dec. 5, 2019

(87) PCT Pub. No.: WO2019/003752
PCT Pub. Date: Jan. 3, 2019

(65) Prior Publication Data
US 2020/0196842 A1 Jun. 25, 2020

(30) Foreign Application Priority Data
Jun. 29, 2017 (EP) .................................... 17178775

(51) Int. Cl.
| A61B 1/00 | (2006.01) |
| A61B 1/045 | (2006.01) |
| G02B 27/42 | (2006.01) |
| H04N 5/225 | (2006.01) |
| H04N 5/232 | (2006.01) |
| A61B 1/313 | (2006.01) |

(52) U.S. Cl.
CPC ...... *A61B 1/00186* (2013.01); *A61B 1/00009* (2013.01); *A61B 1/00039* (2013.01); *A61B 1/045* (2013.01); *G02B 27/4205* (2013.01); *H04N 5/2254* (2013.01); *H04N 5/23203* (2013.01); *A61B 1/00154* (2013.01); *A61B 1/3132* (2013.01); *H04N 2005/2255* (2013.01)

(58) Field of Classification Search
CPC ............ A61B 1/00186; A61B 1/00009; H04N 5/2254; H04N 5/23203; G02B 27/4205
USPC ........................................................ 348/65
See application file for complete search history.

(56) References Cited

U.S. PATENT DOCUMENTS

2018/0052050 A1* 2/2018 Menon ...................... G01J 3/36
2018/0132706 A1* 5/2018 Nagae ................ A61B 1/00188

FOREIGN PATENT DOCUMENTS

| CN | 1550039 A | 11/2004 |
| CN | 102741671 A | 10/2012 |
| WO | 00/13568 A1 | 3/2000 |

(Continued)

OTHER PUBLICATIONS

Office Action issued in Japanese Application PCT/JP2018/020345 dated Oct. 15, 2019.

(Continued)

*Primary Examiner* — On S Mung
(74) *Attorney, Agent, or Firm* — Xsensus, LLP

(57) ABSTRACT

A medical imaging system including: imaging circuitry configured to capture an image; a defractive filter array mounted over the sensor circuitry and a separation device configured to adjust the distance between the defractive filter array and the sensor circuitry.

13 Claims, 7 Drawing Sheets

(56) References Cited

FOREIGN PATENT DOCUMENTS

| WO | 01/28407 A1 | 4/2001 |
| WO | 2007/038787 A1 | 4/2007 |
| WO | 2016/154445 A1 | 9/2016 |
| WO | 2017/043000 A1 | 3/2017 |

OTHER PUBLICATIONS

Cordonier, C.E.J., "Simultaneous Patterning of Independent Metal/Metal Oxide Multi-Layer Films Using Two-Tone Photo-Acid Generating Compound Systems", Nanomaterials, vol. 2, 18 Pages total, (2012).

Wang, P., et al., "Ultra-High-Sensitivity Color Imaging via a Transparent Diffractive-Filter Array and Computational Optics", Optica, vol. 2, No. 11, (7 Pages total), (Nov. 2015).

International Search Report and Written Opinion dated Jan. 29, 2019 for PCT/JP2018/020345 filed on May 28, 2018, 16 pages.

Wang, P. and Menon, R., "Ultra-high-sensitivity color imaging via a transparent diffractive-filter array and computational optics," Department of Electrical and Computer Engineering, University of Utah, Salt Lake City, UT, 84112, Oct. 29, 2015, vol. 2, No. 11, XP002783663, pp. 1-1 (See Abstract).

\* cited by examiner

MEDICAL IMAGING SYSTEM, METHOD AND COMPUTER PROGRAM

CROSS REFERENCE TO RELATED APPLICATIONS

This application is based on PCT filing PCT/JP2018/020345, filed May 28, 2018, which claims the benefit of EP 17178775.7, filed Jun. 29, 2017, the entire contents of each are incorporated herein by reference.

TECHNICAL FIELD

The present disclosure relates to a medical imaging system, method and computer program.

BACKGROUND ART

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

The interpretation of medical images is particularly challenging. One factor is that much of a scene will have a similar red colour due to the colour of blood and soft tissue. Therefore, medical imaging systems that are better able to differentiate colour in the red portion of the spectrum, for example, by having a higher number of small spectral bands, are likely to be advantageous.

It is an aim of the present disclosure to address at least these issues.

CITATION LIST

Non Patent Literature

[NPL 1] 'Ultra-High-Sensitivity Color Imaging via a Transparent Diffractive-Filter Array and Computational Optics', Peng WANG and Rajesh MENON. Optica Vol. 2, No. 11/November 2015 pp 933-939

[NPL 2] 'Simultaneous Patterning of Independent Metal/Metal Oxide Multi-Layer Films Using Two-Tone Photo-Acid Generating Compound Systems', Christopher E. J. Cordonier and Hideo Honma. Nanomaterials 2012, 2, 312-328; doi: 10.3390/nano2040312 ISSN 2079-4991

SUMMARY

According to a first aspect, there is provided a medical imaging system including: imaging circuitry configured to capture an image; a diffractive filter array mounted over the sensor circuitry and a separation device configured to adjust the distance between the diffractive filter array and the sensor circuitry.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings.

DESCRIPTION OF EMBODIMENTS

Figure 1:
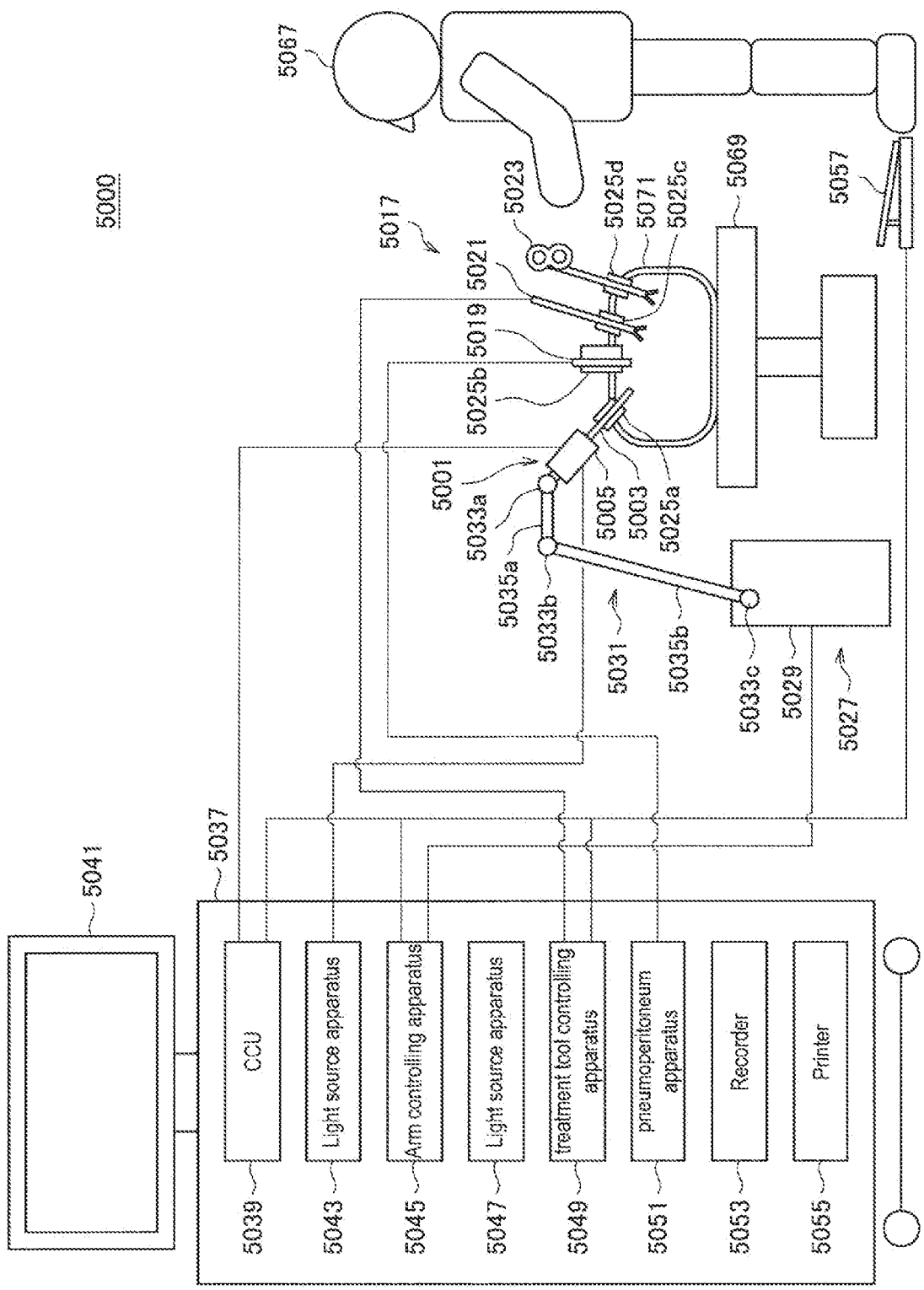
FIG. 1 is a view depicting an example of a schematic configuration of an endoscopic surgery system.

Referring now to the drawings, wherein like reference numerals designate identical or corresponding parts throughout the several views.

1. Application

<<1. Application>>

The technology according to an embodiment of the present disclosure can be applied to various products. For example, the technology according to an embodiment of the present disclosure may be applied to an endoscopic surgery system.

FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body lumens of the patient 5071 through the trocars 5025a to 5025d. In the example depicted, as the other surgical tools 5017, a pneumoperitoneum tube 5019, an energy treatment tool 5021 and forceps 5023 are inserted into body lumens of the patient 5071. Further, the energy treatment tool 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, a pair of tweezers or a retractor may be used.

An image of a surgical region in a body lumen of the patient 5071 imaged by the endoscope 5001 is displayed on a display apparatus 5041. The surgeon 5067 would use the energy treatment tool 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy treatment tool 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body lumen of the patient 5071, and a camera head 5005 connected to a proximal end of the lens barrel 5003. In the example depicted, the endoscope 5001 is depicted which includes as a hard mirror having the lens barrel 5003 of the hard type. However, the endoscope 5001 may otherwise be configured as a soft mirror having the lens barrel 5003 of the soft type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body lumen of the patient 5071 through the objective lens. It is to be noted that the endoscope 5001 may be a direct view mirror or may be a perspective view mirror or a side view mirror.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy treatment tool 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy treatment tool 5021 for cautery or incision of a tissue, sealing of a blood vessel or the like. A pneumoperitoneum apparatus 5051 feeds gas into a body lumen of the patient 5071 through the pneumoperitoneum tube 5019 to inflate the body lumen in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 1, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body lumen of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the surgery room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrowband light and/or excitation light suitable for special light observation as described above.

(Camera Head and CCU)

Figure 2:
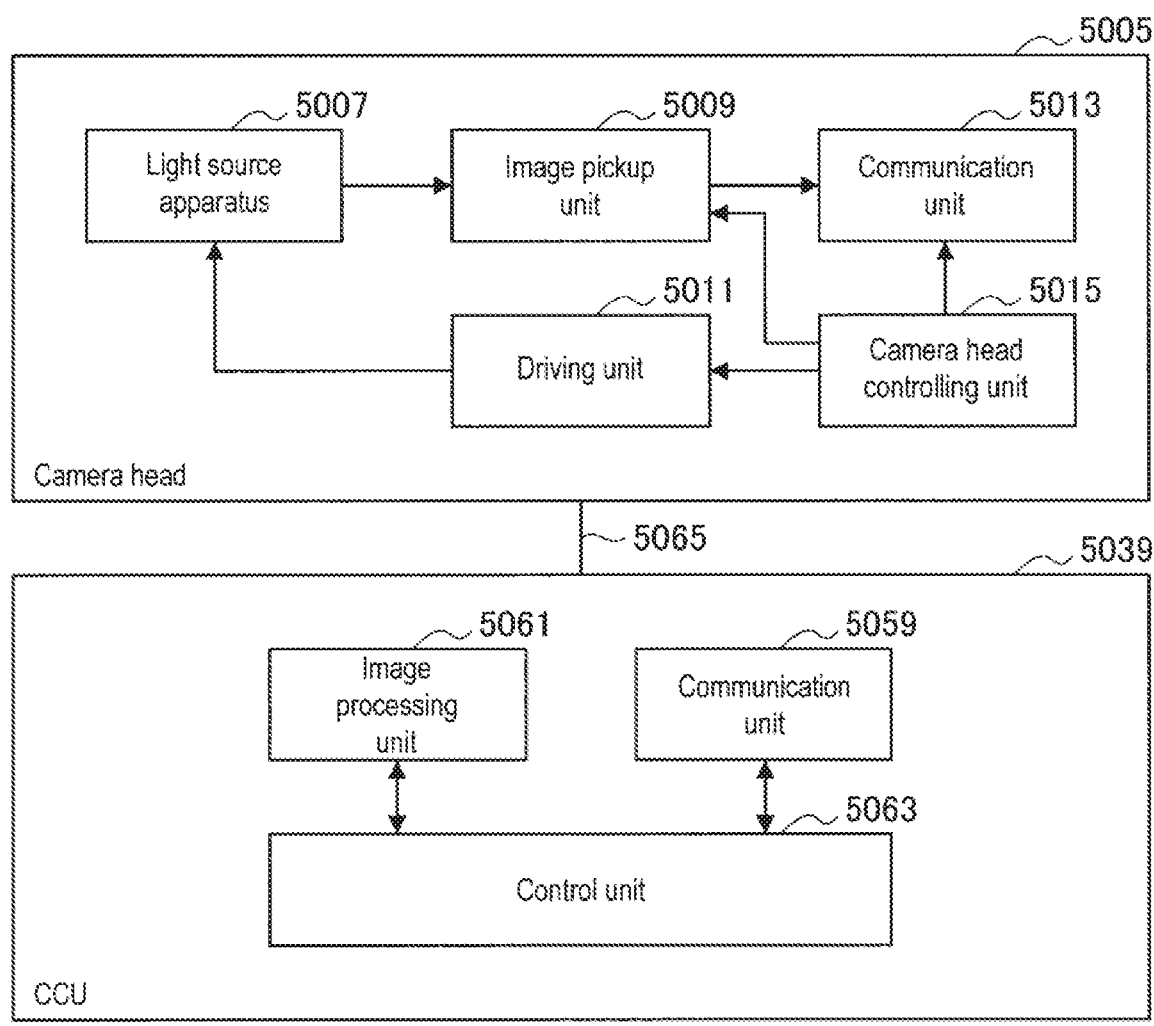
FIG. 2 is a block diagram depicting an example of a functional configuration of a camera head and a camera control unit (CCU) depicted in FIG. 1.

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in colour. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF)

function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy treatment tool 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the surgery room. Therefore, such a situation that movement of medical staff in the surgery room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a soft endoscopic system for inspection or a microscopic surgery system.

The technology according to an embodiment of the present disclosure can be applied suitably to the control unit 5063 from among the components described hereinabove. Specifically, the technology according to an embodiment of the present disclosure relates to endoscopy and/or microscopy or any kind of medical imaging. By applying the technology according to an embodiment of the present disclosure to the endoscopy and/or microscopy technology and/or medical imaging more generally, the granularity of the shades of red can be improved and therefore distinguishing objects during endoscopy is easier. This reduces the likelihood of injury or death of a patient and improves the efficiency with which the medical procedure (such as surgery) can be carried out.

In order to improve the granularity of the shades of red of an endoscopy image, it is known that multispectral and hyperspectral imaging is useful in some forms of endoscopy. This is because multi-spectral imaging splits the spectrum into many spectral bands, and hyperspectral splits the spectrum further still.

Such techniques have the advantage that certain materials emit or reflect light at a specific frequency, or small range of frequencies. Therefore by having a more granular detection these materials can be identified. However, if just red, green and blue bands were used (as in Bayer Filters) then their identification might be masked by the amount of various shades of red.

Consequently, hyperspectral imaging and multi-spectral imaging is known to be advantageous for some forms of endoscopic imaging.

Although [NPL 1] does not mention applying hyperspectral imaging and multi-spectral imaging to medical and endoscopic imaging, one mechanism for hyperspectral imaging in general is provided in [NPL 1].

In this system, Diffractive Filter Arrays (DFAs) are used. DFAs are known to the skilled person and consist of a layer of material where the diffraction of light varies across its surface. Such filters allow all the light to pass, hence have improved sensitivity over Bayer filters. In [NPL 1] it is shown that DFAs are easily fabricated, being fabricated in one layer, and with a large tolerance to fabrication inaccuracy. This reference also shows DFAs can be used as a 'snapshot' hyperspectral imager.

The device created in [NPL 1] has the DFA placed in front of a standard panchromatic image sensor. The DFA and the image sensor is separated by a distance 'd'. The device is first characterized by applying known wavelengths of light to the device and measuring its response, thus creating a 'spatial-spectral point spread function' (i.e. finding the image sensor's response to a known 'scene'). This information is then used to solve the inverse problem (i.e. finding the 'scene' with a known image sensor response), whereby the reading of the image sensor is used in combination with the spatial-spectral point spread function to estimate the scene.

However, the inventors of the present disclosure have identified a problem with the device in [NPL 1]. The device is sensitive to the distance 'd' as (i) spatial resolution improves as d is made smaller, whereas (ii) the spectral resolution is degraded due to cross-talk between pixels as d is made smaller.

Hence having a fixed distance 'd' as in [NPL 1] creates a compromise between spectral and spatial resolution.

This is a problem, especially in the field of medical imaging where the surgeon requires a high degree of spatial resolution to avoid injury to a patient by cutting vasculature or tissue. For example, in a laparoscopic surgery, endoscopic images typically contain lots of red portion and the surgeon has to discriminate different red colours in the image to analyse the image. Also in the surgical operation using monitors, high-resolution images (such as 4K or 8K) are really demanded. This is to improve surgical efficiency. So an endoscope with high spectral resolution and high spatial resolution is highly demanded in the use of any medical imaging such as a surgical operation.

This problem is addressed by the present disclosure.

Figure 3A:
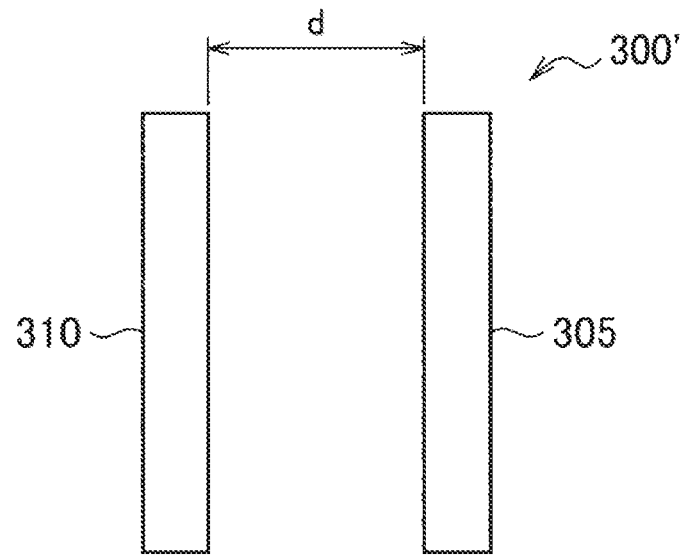
FIG. 3A shows a lens arrangement.

In FIG. 3A, a DFA and image sensor arrangement according to [NPL 1] is shown. This arrangement 300' has a DFA 305 separated from an image sensor 310 by a distance 'd'.

In embodiments, the image sensor 310 detects light energy on a spatial array, and converts this to an electrical signal, thus creating a record of the scene from where the light energy was directed.

In embodiments, the image sensor 310 is a Charge Coupled Device (CCD) or CMOS sensor.

Figure 3B:
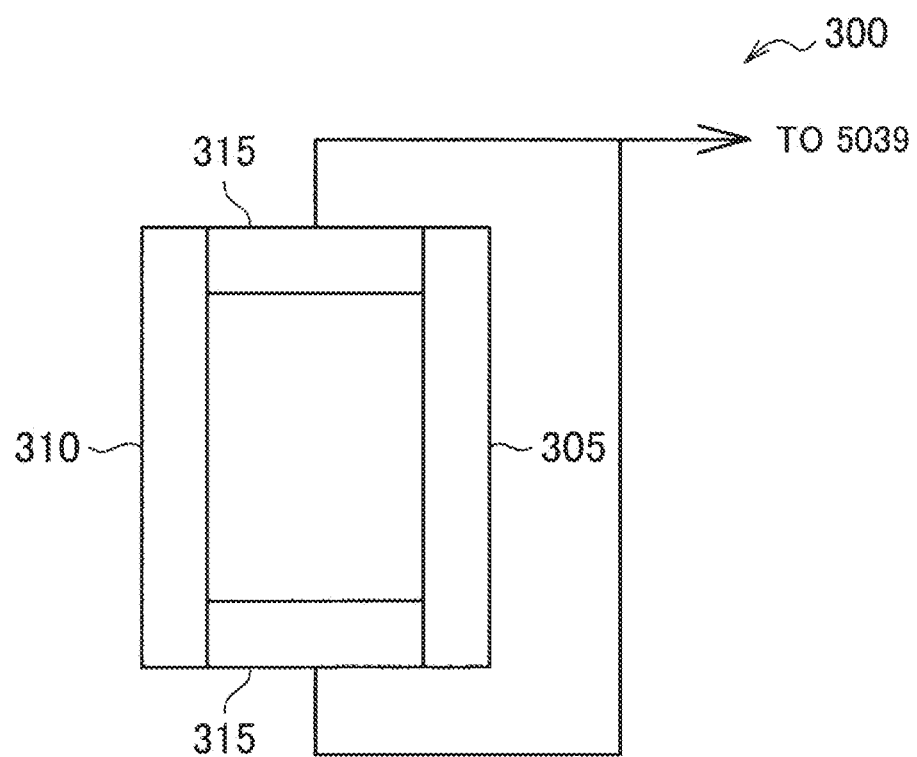
FIG. 3B shows a lens arrangement according to embodiments of the disclosure.
Figure 3C:
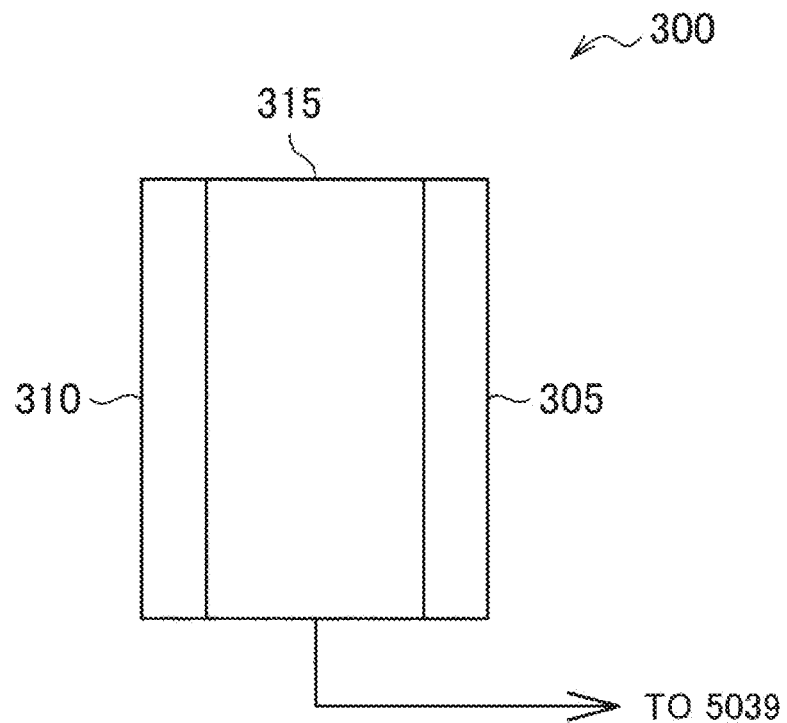
FIG. 3C shows a lens arrangement according to embodiments of the disclosure.

In FIG. 3B and FIG. 3C, embodiments of the disclosure are shown. Specifically, in FIGS. 3B and 3C, a DFA and image sensor arrangement 300 the image sensor 310 and the DFA 305 are separated by a distance. However, unlike in the arrangement 300' of FIG. 3A, the arrangement 300 in FIG. 3B includes a separation unit 315 between the image sensor 310 and the DFA 305. The separation unit 315 is mounted onto the image sensor 310 or the DFA 305 or mounted onto both the image sensor 310 and the DFA 305. Importantly, the purpose of the separation unit 315 is to adjust the distance between the image sensor 310 and the DFA 305. In other words, the separation unit 315 may be provided in any configuration to allow the distance between the image sensor 310 and the DFA 305 to be adjusted.

In embodiments, the separation unit 315 is connected to the CCU 5039 which controls the separation unit 315 to adjust the distance between the image sensor 310 and the DFA 305.

It is envisaged that the image sensor arrangement 300 in FIGS. 3B and 3C will be located in either the endoscope or the head unit of the endoscope. Of course, in the general case of a medical imaging system, the image sensor arrangement 300 may be likewise located anywhere in an appropriate position.

In the specific arrangement 300 of FIG. 3B, the separation unit 315 is located around the perimeter of the image sensor 310. In other words, the separation unit 315 frames the image sensor 310 and/or the DFA 305. This means that there is a gap between the image sensor 310 and the DFA 305. This gap is filled with air or another gas. Accordingly, in this embodiment, the separation unit 315 may or may not be made of transparent material.

On the other hand, in the specific arrangement 300 of FIG. 3C, the separation unit 315 covers the image sensor 310 and/or the DFA 305. This means that the gap between the image sensor 310 and the DFA 305 is filled with the separation unit 315. In this instance, the separation unit 315 will need to be made by transparent, or at least substantially transparent, material. This provides strength as the gap between the image sensor 310 and the DFA 305 is filled with a transparent, and probably non-gaseous, material.

Of course the disclosure is not so limited to the two arrangements of FIGS. 3B and 3C. The separation unit 315 may be a lattice arrangement. Of course, the gap between the image sensor 310 and the DFA 305 may include another material which can provide support whilst expanding and contracting as the separation between the DFA 305 and the image sensor 310 changes. One example may include a gel.

The separation unit 315 may be made from any material whose size changes in a controllable manner. For example, the separation unit 315 may be made from piezoelectric materials. These known materials are materials that change stress within their volume when a voltage is applied. Additionally or alternatively, the separation unit 315 may be made from Electroactive polymers (EAP). These are polymers that exhibit a change in shape or size when stimulated by an electric field.

Figure 4A:
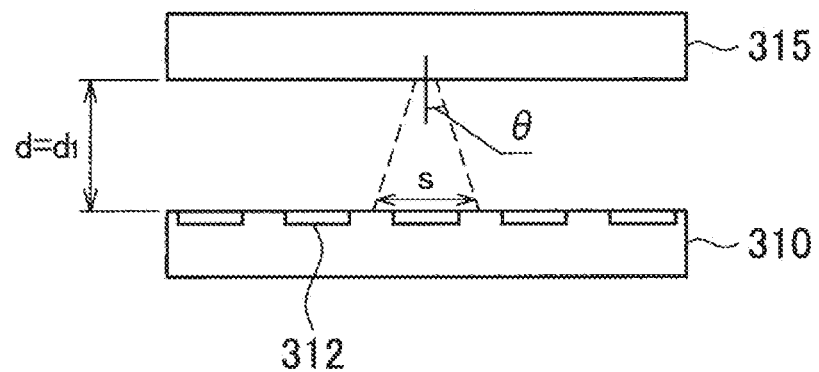
FIG. 4A shows another view of the lens arrangement according to embodiments of the disclosure.
Figure 4B:
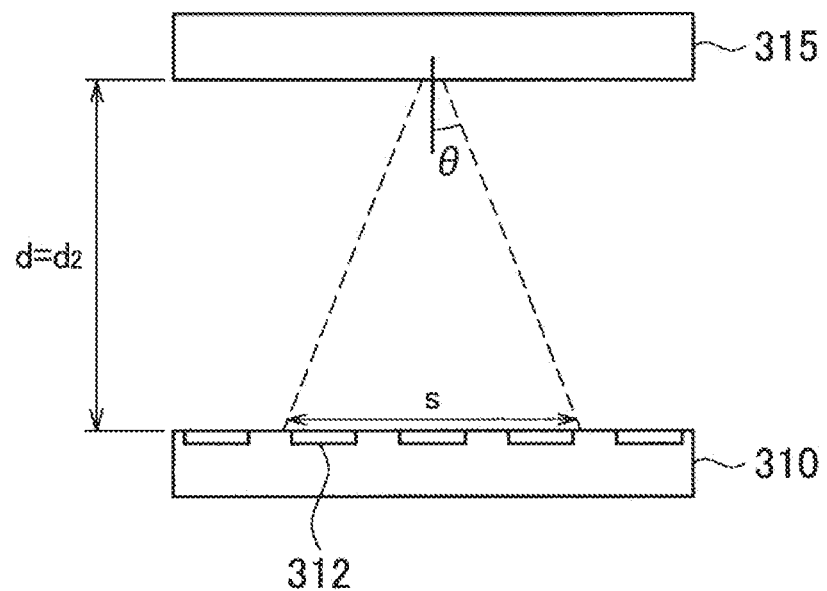
FIG. 4B shows another view of the lens arrangement according to embodiments of the disclosure.

Referring to FIGS. 4A and 4B, an explanation of the interaction of the DFA 305, the image sensor 310 and the distance, d, separating the DFA 305 and the image sensor 310 is given.

In FIGS. 4A and 4B, the image sensor 310 includes pixels 312 which extend along the surface of the image sensor 310. The DFA 315 is composed of many facets, each facet bending the light by a specified angle. In the example of FIGS. 4A and 4B, the same facet bends the light by 0° to the vertical.

The difference between FIGS. 4A and 4B is the separation distance, d, between the image sensor 310 and the DFA 305. Specifically, in FIG. 4A, the separation distance d=d1 and in FIG. 4B, the separation distance d=d2, where d1 is less than d2.

This difference in separation distance between the image sensor 310 and the DFA 305, for any value of θ, has the effect of spreading the light over a different number of pixels 312 on the image sensor 310. This is demonstrated in FIG. 4A, where the light through the facet is spread, s, over a single pixel and in FIG. 4B, where the light through the facet is spread, s, over 3 pixels.

This means that in FIG. 4A, as the light is detected by only a single pixel, the spatial resolution of the image is high. This is because it is possible to correlate the position of the light through the facet to the corresponding pixel.

On the other hand, in FIG. 4B, as the light is detected by 3 pixels, the spatial resolution of the image is low. However, as the light is spread over 3 pixels, and the amount the light bends is related to the frequency of the light, the spectral resolution of the image is high.

As the DFA separation distance increases the light spread function of the DFA (which relates to the colour spread of the light at that pixel) increases in size, spreading the light that arrived at one point in the first face of the DFA over a larger area of pixels. This makes it harder and harder to reconstruct a good spatial representation of the scene. The process is continuous. A maximal DFA separation is selected which results in at least a reasonable ability to reconstruct some kind of spatial image.

The mechanism for reconstructing the image from this spread is described in [NPL 1] and so will not be repeated here for brevity.

More generally, the system may operate in a first mode when the distance between the diffractive filter array and the imaging circuitry is at or below a predetermined distance and to operate in a second mode when the distance between the diffractive filter array and the imaging circuitry is above the predetermined distance.

Figure 5A:
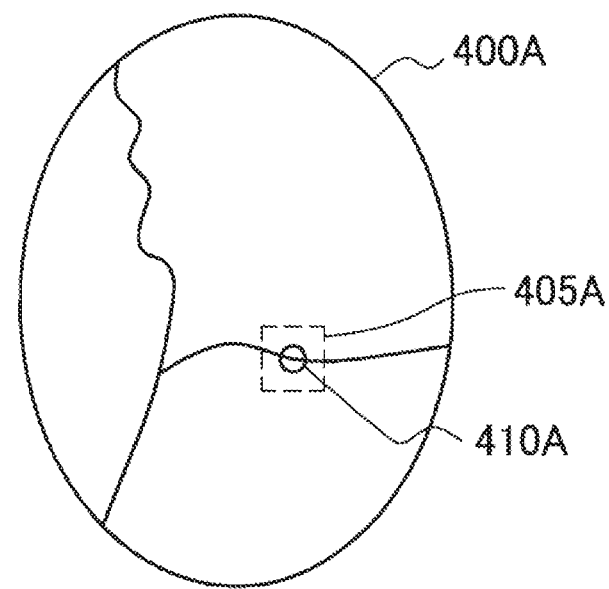
FIG. 5A shows an endoscope view according to embodiments of the disclosure.
Figure 5B:
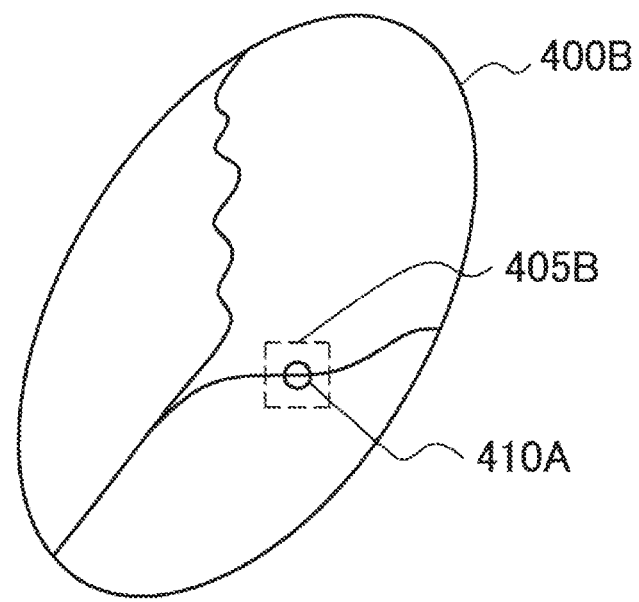
FIG. 5B shows an endoscope view according to embodiments of the disclosure.

Referring to FIG. 5A and FIG. 5B an example of endoscope views according to embodiments of the disclosure are shown. Specifically, the endoscope view 400A in FIG. 5A shows an object of interest 410A. This object of interest may be a polyp, tumour, growth, lesion or any kind of object that may of interest to the surgeon. It is envisaged that the term object may also include edges between materials, for example, between soft tissue and bone. This object may be detected using an object detection algorithm or an edge detection algorithm. As will be explained later, this detected object may be used to align a high spectral resolution image and a high spatial resolution image. In addition, detection of the object may trigger the capture of the high spectral resolution image and the high spatial resolution image.

The object 410A may be identified by the user of the medical imaging system using a user interface. In this instance, or the instance that the object 410A is automatically detected by the system, the display may include a highlighted region 405A which, in this case, is a box (but the disclosure is not so limited) to highlight the object 410A to the user.

Once the object has been identified, a high spectral resolution image and/or a high spatial resolution image of the endoscope view, or the object is captured. FIG. 5A shows a high spectral resolution image of the endoscope view and FIG. 5B shows a high spatial resolution image of the endoscope view.

Figure 6:
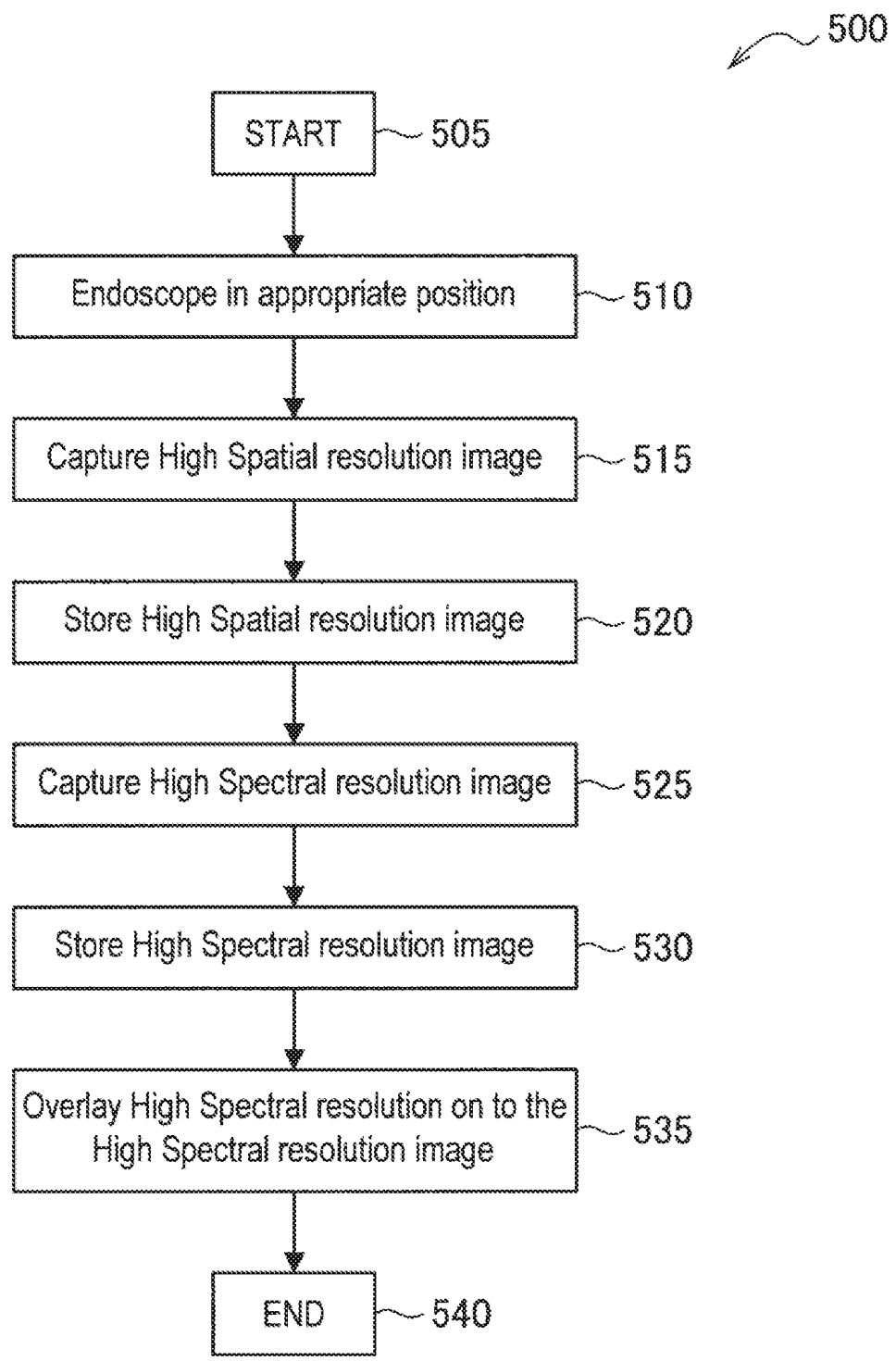
FIG. 6 shows a flow diagram according to embodiments of the disclosure.

Referring to FIG. 6, a flowchart 500 explaining the operation of systems according to embodiments is described.

The process starts at step 505.

In step 510, the endoscope or, more generally, the medical imaging probe is located at the appropriate position within the patient's body. In the example of FIG. 5A and FIG. 5B the endoscope is determined to be in the appropriate position because the endoscope view includes the object 410A and 410B.

In response to being in the appropriate position, a high spatial resolution image is captured. This is step 515. In order to capture the high spatial resolution image, the CCU 5039 controls the separation between the DFA 305 and the image sensor 310. The separation is controlled by applying a control signal such as an electric signal or an electric field control signal to the separation unit 315. The appropriate distance is determined according to the spatial resolution required which may be determined by the surgeon in advance or the distance of the medical probe from the object of interest and the type of light source provided on the medical probe. These values of separation, d, will be calculated in advance during manufacture of the product.

After the CCU 5039 controls the separation unit 315 to achieve the desired separation between the image sensor 310 on the DFA 305, the image is captured in step 515 and stored in step 520.

The process then moves step 525 where a high spectral resolution image is captured. In a similar manner to that for the high spatial resolution, the CCU 5039 determines the outer separation required between the image sensor 310 and the DFA 305. This information is provided during manufacture and will take account of ambient lighting condition within the patient and the distance between the probe and the object of interest. The captured image is then stored in step 530.

In order to allow the user to benefit from a high spatial resolution and a high spectral resolution image, the stored high spectral resolution image and the stored spatial resolution image are overlaid upon one another. In order to determine the appropriate pixel correspondence so that the two images are properly overlaid upon one another, one of several methods may be implemented.

One example method may be the high spatial image is assessed using an edge detection algorithm, for example, an implementation of the Canny Edge detection algorithm. This creates a set of lines within the high spatial resolution image. These are then used to create a new image. The high spectral image is then aligned with this new image by using an edge detection algorithm on the high spectral image to find edges of distinct spectral change. It should be noted that some parts of the scene will contain structure that is visible to the eye (and thus also contained in the high spatial image) and the high spectral image. An example of this is a border between bone and soft tissue.

Other regions of the image may have structure that is visible in either of the high spatial resolution image or the high spectral resolution image and not the other. For example, if blood is lying over another material it is possible that only the form of the blood is visible and the high spatial image where the form of the underlying structure is also visible in the high spectral resolution image. Therefore, not all high spectral edges will have corresponding high spatial edges. The high spatial edges are recorded in a manner that means that there location in the high spectral image is known. In other words, once an alignment between the high spectral edges and the high spatial edges has been made, the high spectral edges can be replaced by the high spectral image in the same location.

A subset of the high spectral edges that are closest correlated to the high spatial edges is found. Note that the purpose of the high spectral edges is to align the two images. Therefore, for 2D images, only two points of reference are required and for a 3D image 3 points of reference are required. Typically, rather than using a specific point, to increase the accuracy of the alignment, a section line will be used. Accuracy is further increased if these sections have a sufficient separation within the image. This can be realised by considering the greater accuracy possible where two sections of the 2D image are used which are in corners of the image verses the two sections being close together in the centre of the image. Hence an optimisation is possible whereby the minimum number of points that have sufficient size, and separation as chosen to align the image.

These closely correlated high spectral edges are added to the immediate image as a layer in the image and aligned to the high spatial resolution edges. The high spectral edges are then removed from the image being replaced by the high spectral image, with the final image the including the high spatial edges and the aligned high spectral image. The final image is then viewed by the user on the display.

The process then ends at step 540.

As noted above, one trigger to perform the capture of high spatial and/or spectral resolution images is the detection of an object in the image. However, the disclosure is not so limited. For example, the surgeon can trigger the capture of the high spectral and/or spatial resolution images using a User Interface or the like.

Another mechanism for triggering the capture of the high spectral and/or high spatial resolution images includes a capturing the image in response to a predetermined sensor output. In this additional mechanism, the sensor may be a gyroscope or accelerometer (or any kind of appropriate sensing circuitry) located in the medical imaging system. Typically, the sensor circuitry detects whether the probe or at least the image sensor (which may be an endoscope tip) is stationary. This indicates that the surgeon is carefully reviewing a particular area and a high spatial and/or spectral resolution image may be useful. Of course, other sensors are envisaged such as an environmental sensor, such as a temperature sensor, which may provide a particular temperature profile of an area indicating a high spectral resolution image and/or a high spatial resolution image is required. An appropriate temperature profile might include a high localised temperature at the area of interest.

The sensor output is compared with a database of predetermined sensor outputs which are used to trigger the capture of the high spatial and/or spectral resolution image. In the event of a match, or where the captured sensor output is within a predetermined range from the stored high spatial and/or spectral resolution image, then the high spatial and/or spectral resolution image is captured.

Other variants include capturing the high spatial and/or spectral resolution image only when useful for the viewing of endoscopic or medical images.

Specifically, images associated with one mode of operation may be captured predominately. For example, only high spatial resolution images may be captured. These may be displayed to the user. In the event that the user believes that there is an object of interest, the user may switch to a second mode. In this instance, the high spectral resolution image may also be captured. In other words the control circuitry is configured to capture a plurality of images in either the first mode or the second mode and an image in the other mode and overlay the image captured in either the first mode or the second mode and the image in the other mode when a predefined object is present in both captured images. The images may then be overlaid and displayed as explained with reference to FIG. 6.

Although the foregoing mentions the user switching to a second mode, the disclosure is not so limited. Specifically, the image captured in the first mode may be compared to stored images which may identify triggers of interest. For example, certain configurations of blood vessels may be stored within a database and identified during the medical imaging process. When such configurations are identified, this may be used as a trigger to capture the high spectral resolution image.

Of course, although the foregoing mentions the first mode being a predominant capture of high spatial resolution images, the disclosure is not so limited and the first mode may be a predominant capture of high spectral resolution images, with the second mode being a capture of high spatial resolution images. In this case, a trigger may be where the spectral content of the image changes rapidly. This may indicate a bleed point or the like and a high spatial resolution image may be captured as a result.

A system according to any preceding claim configured to operate in a first mode when the distance between the diffractive filter array and the imaging circuitry is at or below a predetermined distance and to operate in a second mode when the distance between the detractive diffractive filter array and the imaging circuitry is above the predetermined distance.

In embodiments, the trigger for capturing high spatial resolution images may occur when a zoom is used. This is because application of a zoom indicates that a high spatial resolution is required.

In embodiments, the arrangement 300' should be suitable for autoclaving. As the skilled person appreciates, autoclaving is a term of art that means to heat in an autoclave. This sterilises the arrangement 300'.

In order to achieve this, the DFA 305 can be made from a ceramic material such as a metal oxide or a glass that can survive high temperature. In [NPL 1], a patterning process is applied to glass using photoresist and etching of the glass then takes place. In the instance of the DFA 305 being a metal oxide (such as zinc or indium oxide), a patterning and etching process as explained in [2] may be used. Of course, the disclosure is not so limited. Specifically, the DFA 305 may be a polymer such as plastic which may be sealed in a glass enclosure to protect the DFA 305 from the heat of an autoclave.

It is possible that the sensitivity of the image sensor 310 and the transmissivity of the DFA 305 may change over time. In order to address this, known image target and illumination source settings will be used to calibrate the algorithm of [NPL 1].

In embodiments of the disclosure, the lighting of the area of interest may be altered. This may improve the spatial resolution of the high spatial resolution image. For example, for a particular value of separation, d, different colours exhibit a different degree of spatial resolution.

This is because the distance d changes the ability to resolve spectral colours and spatial images. To maximise (or at least increase) spatial resolution d is set to zero. However, then all the colours of a point in the image are collected by one pixel, so there is no spectral resolution. A larger distance d separates the colour from each other, but there is a potential for spatial confusion, depending on the scene and the colours.

Therefore, the optimal setting of d (to jointly maximise spatial and spectral resolution) will depend on the image (its spatial and spectral distribution).

One method of getting to the correct value of d is to start with d at zero and then increase the separation d until the reconstructed spatial resolution falls to a predetermined value. This may be a minimum value. The resulting spectral information is then above a threshold (for example, the maximum). This spectral information is the largest possible whilst maintaining a certain spatial resolution.

To increase the spatial resolution of the image, whilst maintaining knowledge of spectral response, it is useful to have light sources which consist of a number of narrow bands in the lighting. This is opposed to light with a continuous spread of wavelengths. The narrow band light is light such as provided by LEDs or lasers. In this way, the corresponding transformed image produced by each spectral light source is kept spatially confined. This is because each colour generates a focused image and this enables better extraction of the original spatial distribution of the light. In addition, the correlation of colours in an image depends on, for example, the materials observed within the image. This means that the correlation of colours is image specific. So, if illumination is appropriately controlled, the set of colours that are reflected from the scene are restricted. This is useful for separating the spatial and spectral information. This will also depend on the actual structure of the DFA selected, in that the diffractive structures in the DFA will spread light of specific wavelengths in certain directions and angles and this will depend on the DFA. In general, of course, similar colours behave roughly the same (they are redirected at similar angles and directions), but with their angle of spread being a function of their wavelength, at least for a range of colours.

The distance (d) is optimised for all the colours in an image and the different bands do not require specific optimisation.

If the distance is varied during capturing endoscopic video image, such information (distance d or information indicating spatial/spectral resolution) is recorded/outputted with the video as a metadata.

The spectral resolution can be controlled such that spectral resolution is improved in only a particular wavelength area (red or near infrared).

Various embodiments of the present disclosure are defined by the following numbered clauses:

1. A medical imaging system including: imaging circuitry configured to capture an image; a diffractive filter array mounted over the sensor circuitry and a separation device configured to adjust the distance between the diffractive filter array and the sensor circuitry.

2. A system according to clause 1, further including control circuitry, wherein under the control of the control circuitry, the separation device is configured to change shape.

3. A system according to clause 2, wherein the separation device is made from either piezoelectric material or electroactive polymer.

4. A system according to any preceding clause, wherein the separation device is a frame upon which the diffractive filter array is mounted and which is configured to surround the imaging circuitry.

5. A system according to any one of clause 1 to 3, wherein the separation device is transparent and mounted onto the imaging circuitry.

6. A system according to any preceding clause configured to operate in a first mode when the distance between the diffractive filter array and the imaging circuitry is at or below a predetermined distance and to operate in a second mode when the distance between the diffractive filter array and the imaging circuitry is above the predetermined distance.

7. A system according to clause 6, wherein the control circuitry is configured to: capture an image in the first mode; capture an image in the second mode; and overlay the image captured in the first mode onto the image captured in the second mode.

8. A system according to clause 6, wherein the control circuitry is configured to: capture a plurality of images in either the first mode or the second mode and an image in the other mode and overlay the image captured in either the first mode or the second mode and the image in the other mode when a predefined object is present in both captured images.

9. A system according to any preceding clause, further including sensor circuitry configured to determine the movement of the imaging sensor and the imaging circuitry is configured to capture the image when the sensor circuitry determines a predefined movement of the imaging sensor.

10. A system according to any preceding clause, further including a User Interface, wherein the imaging circuitry is configured to capture the image in response to a user input on the user interface.

11. A medical imaging method including: capturing an image; and adjusting the distance between a diffractive filter array and imaging circuitry mounted thereover.

12. A method according to clause 11, including changing the shape of a separation device used to adjust the distance between the diffractive filter array and the sensor circuitry.

13. A method according to clause 12, wherein the separation device is made from either piezoelectric material or electroactive polymer.

14. A method according to either clause 12 or 13, wherein the separation device is a frame upon which the diffractive filter array is mounted and which is configured to surround the imaging circuitry.

15. A method according to either one of clause 12 or 13, wherein the separation device is transparent and mounted onto the imaging circuitry.

16. A method according to any one of clause 11 to 15 including operating in a first mode when the distance between the diffractive filter array and the imaging circuitry is at or below a predetermined distance; and operating in a second mode when the distance between the diffractive filter array and the imaging circuitry is above the predetermined distance.

17. A method according to clause 16, including: capturing an image in the first mode; capturing an image in the second mode; and overlaying the image captured in the first mode onto the image captured in the second mode.

18. A method according to clause 16, including: capturing a plurality of images in either the first mode or the second mode and an image in the other mode and overlaying the image captured in either the first mode or the second mode and the image in the other mode when a predefined object is present in both captured images.

19. A method according to any one of clause 11 to 18, further including determining the movement of the imaging circuitry and the imaging circuitry is configured to capture the image when a predefined movement of the imaging circuitry is determined.

20. A method according to any one of clause 11 to 19, further including capturing the image in response to a user input on a user interface.

21. A computer program product including computer readable code which, when loaded onto a computer, configures the computer to perform a method according to any one of clause 11 to 20.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. A medical imaging system including:
a sensor configured to capture an image;
a diffractive filter array mounted over the sensor; and
a separator configured to adjust a distance between the diffractive filter array and the sensor, wherein the system is configured to operate in a first mode when the distance between the diffractive filter array and the sensor is at or below a predetermined distance to generate a high spatial resolution image and to operate in a second mode when the distance between the diffractive filter array and the sensor is above the predetermined distance to generate a high spectral resolution image.

2. The system according to claim 1, further including control circuitry, wherein under control of the control circuitry, the separator is configured to change shape.

3. The system according to claim 2, wherein the separator is made from either piezoelectric material or electroactive polymer.

4. The system according to claim 1, wherein the separator is a frame upon which the diffractive filter array is mounted and which is configured to surround the sensor.

5. The system according to claim 1, wherein the separator is transparent and mounted onto the sensor.

6. A medical imaging method, the method comprising:
capturing an image using a sensor and a diffractive filter array mounted over the sensor;
adjusting a distance between the diffractive filter array and the sensor;
operating in a first mode when the distance between the diffractive filter array and the sensor is at or below a predetermined distance to generate a high spatial resolution image; and
operating in a second mode when the distance between the diffractive filter array and the sensor is above the predetermined distance to generate a high spectral resolution image.

7. The method according to claim 6, including changing a shape of a separator used to adjust the distance between the diffractive filter array and the sensor.

8. The method according to claim 7, wherein the separator is made from either piezoelectric material or electroactive polymer.

9. The method according to claim 7, wherein the separator is a frame upon which the diffractive filter array is mounted and which is configured to surround the sensor.

10. The method according to claim 7, wherein the separator is transparent and mounted onto the sensor.

11. A non-transitory computer product readable storage device including computer readable code which, when read by a computer, causes the computer to perform a method according to claim 6.

12. The method according to claim 6, wherein adjusting the distance between the diffractive filter array and the sensor includes maintaining focus of the image on the sensor.

13. The system according to claim 1, wherein system is configured to maintain focus of the image on the sensor while adjusting the distance between the diffractive filter array and the sensor.

* * * * *